United States Patent
Mandeville, III et al.

(10) Patent No.: US 6,187,762 B1
(45) Date of Patent: *Feb. 13, 2001

(54) POLYVALENT POLYMERS FOR THE TREATMENT OF ROTAVIRUS INFECTION

(75) Inventors: W. Harry Mandeville, III, Lynnfield; John S. Petersen, Acton; Venkata R. Garigapati, Waltham; Thomas X. Neenan, Boston, all of MA (US)

(73) Assignee: GelTex Pharmaceuticals, Inc., Waltham, MA (US)

( * ) Notice: Under 35 U.S.C. 154(b), the term of this patent shall be extended for 0 days.

This patent is subject to a terminal disclaimer.

(21) Appl. No.: 09/286,351

(22) Filed: Apr. 5, 1999

Related U.S. Application Data

(63) Continuation of application No. 08/717,265, filed on Sep. 20, 1996, now Pat. No. 5,891,862, which is a continuation-in-part of application No. 08/616,294, filed on Mar. 15, 1996, now abandoned.

(51) Int. Cl.[7] ................................................. A61K 31/70
(52) U.S. Cl. ............................ 514/54; 514/23; 514/24; 514/25
(58) Field of Search ............................ 536/1.11, 4.1, 536/22.1, 123, 123.1; 514/53, 23, 24, 25

(56) References Cited

U.S. PATENT DOCUMENTS

| 4,868,289 | 9/1989 | Magnusson et al. | 536/4.1 |
|---|---|---|---|
| 5,034,516 | 7/1991 | Roy et al. | 536/4.1 |
| 5,891,862 | * 4/1999 | Mandeville, III et al. | 514/54 |

FOREIGN PATENT DOCUMENTS

91/08747  6/1991  (WO) .

OTHER PUBLICATIONS

Matrosovich, M.N., "Towards the development of antimicrobial drugs acting by inhibition of pathogen attachment to host cells: a need for polyvalency," *FEBS LET.* 252(1, 2):1–4(1989).

Sparks, M.A., et al., "Neuraminidase–Resistant Hemagglutination Inhibitors: Acrylamide Copolymers Containing a C–Glycoside of N–Acetylneuraminic Acid," *J. of Med. Chem.*, 36(6):778–783 (1993).

Spaltenstein, A. and Whitesides, G.M., "Polyacrylamides Bearing Pendant α–Sialoside Groups Strongly Inhibit Agglutination of Erylthrocytes by Influenza Virus," *J. Am. Chem. Soc.*, 113:686–687 (1991).

Kingery–Wood, J.E., et al., "The Agglutination of Erythrocytes by Influenza Virus is Strongly Inhibited by Liposomes Incorporating an Analog of Sialyl Gangliosides," *J. Am. Chem. Soc.*, 114(18):7303–7305 (1992).

Matrosovich, M.N., et al., "Synthetic polymeric sialoside inhibitors of influenza virus receptor–binding activity," *FEBS LET.* 272(1,2):209–212 (Oct. 1990).

Byramova, N.E., et al., "(Synthesis of Sialic Acid Pseudopolysaccharides by Coupling of Spacer–Connected Neu5Ac With Activated Polymer," *J. Carbohydrate Chem.*, 10(4):691–700 (1991).

Glass, R.I., et al., "Rotavirus Vaccines: Success by Reassortment?," *Science*, 265:1389–1391 (Sep. 1994).

Blacklow, N.R. and Greenberg, H.B., "Viral Gastroenteritis," *N. En. J. Med.*, 325:252–264 (Jul. 1991).

LeBaron, C.W., et al., "Annual Rotavirus Epidemic Patterns in North America," *J. Am. Med. Assoc.*, 264:983–988 (Aug. 1990).

Yolken, R.H., et al., "Sialic Acid Glycoproteins Inhibit In Vitro and In Vivo Replication of Rotaviruses," *J. Clin. Invest.* 79:148–154 (Jan. 1987).

Kiefel, M.J., et al., "Synthesis and Biological Evaluation of N–Acetylneuraminic Acid–Based Rotavirus Inhibitors," *J. Med. Chem.* 39:1314–1320 (1996).

Roy, R., et al., "Solid–phase Synthesis of Dendritic Sialoside Inhibitors of Influenza A Virus Haemagglutinin," *J. Chem. Soc., Chem. Commun.*, :1869–1872 (1993).

Yuen, C.–T., et al., "Novel Sulfated Ligands for the Cell Adhesion Molecule E–Selectin Revealed by the Neoglycolipid Technology Among O–Linked Oligosaccharides on an Ovarian Cystadenoma Glycoprotein," *Biochemistry*, 31:9126–9131 (1992).

(List continued on next page.)

*Primary Examiner*—Elli Peselve
(74) *Attorney, Agent, or Firm*—Hamilton, Brook, Smith & Reynolds, P.C.

(57) ABSTRACT

The present invention includes polymerizable monomers comprising a fucoside moiety. In one embodiment, the monomer has a polymerizable functional group, such as an olefinic bond, to which the fucoside moiety is attached by a spacer group, for example, an alkylene group, or an alkylene group wherein one or more carbon atoms are substituted by heteroatoms, such as oxygen, nitrogen or sulfur atoms. The present invention also includes polymers comprising one or more fucoside moieties, such as pendant fucoside moieties, which can inhibit or prevent rotavirus infection in a mammal. Such a polymer can comprise, for example, a monomer of the present invention. The polymer can be a homopolymer or a copolymer, and can have, for example, a polyacrylamide, polyacrylate or polystyrene backbone. In another embodiment, the present invention comprises a method for treating a rotavirus infection in a mammal, for example, a human, by administering to the mammal a therapeutically effective amount of a polymer comprising one or more glycoside moieties, such as pendant glycoside moieties. The glycoside moieties can be, for example, fucoside moieties or sialic acid moieties. The polymer can be a homopolyrner or a co-polymer. In one embodiment, the polymer is a copolymer comprising a glycoside-bearing monomer and a hydrophobic monomer. In another embodiment, the polymer to be administered comprises two or more different glycoside-bearing monomers.

21 Claims, No Drawings

OTHER PUBLICATIONS

Sigal, G.B., et al., "Polyacrylamides Bearing Pendant α–Sialoside Groups Strongly Inhibit Agglutination of Erythrocytes by Influenza Virus: The Strong Inhibition Reflects Enhanced Binding Through Cooperative Polyvalent Interactions," *J. Am. Chem. Society*, 118(6):3789–3800 (Apr. 1996).

Jain, R.K., et al., "Total Synthesis of 3'–O–Sialyl, 6'–O–Sulfo Lewis$^x$, NeuAca2→3(6–O–SO$_3$Na)Galβ 1–→4(Fucα1→3)–GlcNAcβ–OMe: A Major Capping Group of GLYCAM–1," *J. Am. Chem. Soc.*, 116:12123–12124 (1994).

Lamblin, G., et al., "Structure of two sulphated oligosaccharides from respiratory mucins of a patient suffering from cystic fibrosis," *Biochem. J.*, 275:199–206 (1991).

Lubineau, A. and Lemoine, R., "Regioselective Sulfation of Galactose Derivatives Through the Stannylene Procedure. New Synthesis of the 3'–O–Sulfated Lewis$^a$ Trisaccharide," *Tetrahedron Letters*, 35(47):8795–8796 (1994).

Chandrasekaran, E.V., et al., "Ovarian Cancer α1,3–L–Fucosyltransferase," *J. of Biological Chem.*, 267(33):23806–23814 (Nov. 25, 1992).

Reddy, G.V., et al., "Synthesis of Precursors for the Dimeric 3–O–SO$_3$Na Lewis X and Lewis A Structures," *Carbohydrate Research*, 280:261–276 (1996).

Ohmoto, H., et al., "Studies on Selectin Blocker. 1. Structure–Activity Relationships of Sialyl Lewis X Analogs," *J. Med. Chem.*, 39:1339–1343 (1996).

Geyer, H., et al., "Oligosaccharide Pattern of HIV–2 gp 120; Dependence on Host Cells and Virus Isolates," *Complex Carbohydrates in Biology and Medicine*, Abstract U104: pp. 266.

Haynes, P.A. and Cross, G.A.M., "Studies On The Structure And Function Of A Novel Carbohydrate antigen Of Trypanosoma Cruzi," *Complex Carbohydrates in Biology and Medicine*, Abstract U105: p. 266.

Oda, Y., et al., "Structure–Function Studies On Carbohydrate Ligands Of Three Selectins. Modifications To Fucose, Sialic Acid and Sulfate As A Sialic Acid Replacement," *Complex Carbohydrates in Biology and Medicine*, Abstract U106: p. 266.

Linn, P., et al., "Site Specific Chemical Modification Of A Strep–Tococcal Antibody Binding Site," *Complex Carbohydrates in Biology and Medicine*, Abstract U107: p. 266.

Guilbert, B., et al., "Dibutylstannylene Acetals: Useful Intermediates for the Regioselective Sulfation of Glycosides," *Tetraheda: Asymmetry*, 5(11):2163–2178 (1994).

Ragan, J.A. and Cooper, K., "Synthesis Of A Galactose–Fucose Disaccharide Mimic of Sialyl Lewis X," *Biorganic & Medicinal Chemistry Letters*, 4(21):2563–2566 (1994).

Roy, R. and Tropper, F.D., "Synthesis of Antigenic Carbohydrate Polymers Recognized by Lectins and Antibodies," *J. Chem. Soc., Chem. Commun.*:1058–1060 (1988).

Mammen, M., et al., "Effective Inhibitors of Hemagglutination by Influenza Virus Synthesized from Polymers Having Active Ester Groups. Insight into Mechanism of Inhibition," *J. Med. Chem.*, 38:4179–4190 (1995).

Itoh, M., et al., "Suppression of Influenza Virus Infection by an N–Thioacetylneuraminic Acid Acrylamide Copolymer Resistant to Neuraminidase," *Virology*, 212:340–347 (1995).

* cited by examiner

POLYVALENT POLYMERS FOR THE TREATMENT OF ROTAVIRUS INFECTION

RELATED APPLICATIONS

This application is a Continuation of Ser. No. 08/717,265, filed Sep. 20, 1996, now U.S. Pat. No. 5,891,862, which is a Continuation-in-Part of Ser. No. 08/616,294, filed Mar. 15, 1996, now abandoned. The teachings of each of these referenced applications are expressly incorporated herein by reference in their entirety.

GOVERNMENT SUPPORT

The invention described herein was supported in whole or in part by Advanced Technology Program Cooperative Agreement No. 70NANB5H1063 from the National Institute of Standards and Technology. The United States Government has certain rights in the invention.

BACKGROUND OF THE INVENTION

Human rotavirus infection is a major cause of severe diarrhea in infants and young children, afflicting virtually every child at some point in the first several years of life (Glass et al., *Science* 265: 1389–1391 (1994)). The situation is particularly acute in developing countries, where rotavirus infection is responsible for 20–40% of hospitalizations for childhood diarrhea and an estimated 870,000 deaths. (Blacklow et al., *New England J. Med.* 325: 252–264 (1991); LeBaron et al., *J. Am. Med. Assoc.* 264: 983–988 (1990)).

Current methods for treating rotavirus infection are limited to rehydration and replacement of lost electrolytes. No methods for preventing or otherwise inhibiting the infection are currently in clinical use.

There is, thus, a need for an agent or agents capable of preventing infection by rotavirus or inhibiting a rotavirus infection.

SUMMARY OF THE INVENTION

The present invention relates to polymers comprising one or more fucoside moieties which can inhibit or prevent rotavirus infection in a mammal, monomers which can serve as starting materials in the synthesis of such polymers, and methods of use of such polymers in the treatment of rotavirus infection in a mammal.

The monomers of the present invention include polymerizable monomers comprising a fucoside moiety. In one embodiment, the monomer has a polymerizable functional group, such as an olefinic bond, to which the fucoside moiety is attached by a spacer group, for example, an alkylene group, or an alkylene group wherein one or more carbon atoms are substituted by heteroatoms, such as oxygen, nitrogen or sulfuir atoms.

The polymers of the present invention comprise fucoside moieties, such as pendant fucoside moieties. Such a polymer can be a homopolymer or a copolymer, and can have, for example, a polyacrylarnide, polyacrylate or polystyrene backbone. In one embodiment, the polymer is a copolymer comprising a fucoside-bearing monomer and acrylamide. In one embodiment, the polymers of the present invention include copolymers which comprise a glycoside-bearing monomer, a hydrophobic monomer and, optionally, one or more additional monomers, such as neutral hydrophilic monomers. Also included are copolymers which comprise two or more glycoside-bearing monomers, and, optionally, a neutral hydrophilic monomer.

In another embodiment, the present invention includes a method for treating a rotavirus infection in a mammal, for example, a human, by administering to the mammal a therapeutically effective amount of a polymer comprising one or more glycoside moieties, such as pendant glycoside moieties. The glycoside moieties can be, for example, fucoside moieties or sialic acid moieties. The polymer can be a homopolymer or a co-polymer. In one embodiment, the polymer is a copolymer comprising a glycoside-bearing monomer and acrylamide.

The present invention offers several advantages. It provides agents and a method for the treatment and prevention of rotavirus infection, of which there were previously none. In addition the fucoside-bearing polymers incorporate a relatively simple and inexpensive sugar.

DETAILED DESCRIPTION OF THE INVENTION

The present invention is based on the discovery that polymers comprising pendant glycoside, particularly fucoside, moieties can interfere with the attachment of rotavirus to target cells, such as cells lining the intestinal lumen. It has been reported that glycoproteins containing sialic acid groups inhibit rotavirus infection in vitro and in vivo (Yolkin et al., *J. Clin. Invest.* 79: 148–154 (1987)). These glycoproteins are isolated in small quantities, are poorly characterized, and are, therefore, not suitable as agents for the treatment of rotavirus infection. The invention relates to the incorporation of sialic acid, fucose and other related sugars into the side chains of synthetic polymers. This provides polymers with many potential sites of interaction with the virus, thereby binding tightly to the virus via a multiplicity of interactions, referred to herein as the "polyvalent effect" (Matrosovich, *FEBS Letters* 252: 1–4 (1989)).

One aspect of the present invention includes a polymer comprising one or more fucoside moieties, preferably pendant fucoside moieties. The term "pendant", as used herein, refers to a structural component of one or more polymer side chains which is not a part of the polymer backbone. Therefore, polymers of the present invention comprise side chains to which are attached fucoside moieties.

The term "monomer", as used herein, refers to both a molecule comprising one or more polymerizable functional groups prior to polymerization, and a repeating unit of a polymer. A copolymer is said to comprise two or more different monomers. A "fucoside-bearing monomer" is a monomer, either polymerized or unpolymerized, which comprises a fucoside moiety. Upon incorporation into a polymer, a facoside-bearing monomer comprises a pendant fucoside moiety.

The term "glycoside", as used herein, is intended to refer to a carbohydrate residue, such as a residue obtained by removal of a hydrogen atom, for example, a hydroxyl hydrogen atom, from a pyranose or a furanose. Usually, a glycoside is formed by removal of a hydrogen atom from a hydroxyl group bonded to the anomeric carbon of a pyranose or a furanose. The term as used herein, however, also encompasses other types of sugar residues, such as the galactosamino moiety, which is derived from galactosamine by removal of a hydrogen atom of the amino group.

The present invention includes monomers which are starting materials in the synthesis of polymers comprising one or more fucoside moieties. Such a monomer comprises a fucoside moiety linked at the anomeric carbon to a spacer group via an atom, which can be, for example, a carbon atom, or a heteroatom, such as an oxygen, nitrogen or sulfur atom. In a preferred embodiment, the monomer is of Formula I,

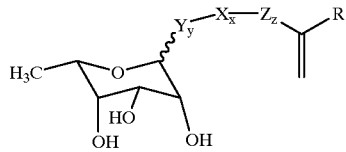
(I)

wherein X is a spacer group and can be a straight chain or branched, substituted or unsubstituted alkylene group, wherein, optionally, one or more carbon atoms are substituted by a heteroatom, such as an oxygen, nitrogen or sulfur atom. Examples include a —(CH$_2$)$_n$— group, wherein n is an integer from about 2 to about 12, a substituted alkylene group, an oxaalkylene group, such as —(CH$_2$)$_2$O[(CH$_2$)$_2$O]$_n$(CH$_2$)$_2$—, wherein n is an integer, or a thiaalkylene group, such as —(CH$_2$)$_n$S(CH$_2$)$_m$—, where n and m are each an integer. The fucoside moiety can be an α- or β-L-fucoside or an α- or β-D-fucoside moiety. This is indicated by the wavy line connecting Y to the sugar moiety in Formula I, which allows for either anomer. The spacer group is attached to the fucoside moiety via Y, which is, for example, a CH$_2$ or NH group, or an oxygen or sulfur atom, and is bonded to the anomeric carbon atom of the fucoside moiety. The spacer group is attached to the polymerizable unit via Z, which can be, for example, an oxygen atom, a phenylene group, an amidocarbonyl group, an oxycarbonyl group, an amino group or an aminomethylene group. The polymerizable unit can be, for example, an olefinic bond. R is a hydrogen atom or a methyl or ethyl group, and x, y, and z are each, individually, 0 or 1.

Additional examples of fucoside-bearing monomers of the present invention are of Formula II and Formula III, shown below. In Formula II, X is a spacer group, such as a straight chain or branched, substituted or unsubstituted alkylene group, wherein, optionally, one or more carbon atoms are substituted by a heteroatom, such as an oxygen, nitrogen or sulfur atom. Examples include a polymethylene group, such as —(CH$_2$)$_n$—, wherein n is an integer from about 2 to about 12, an oxaalkylene group, such as —(CH$_2$)$_2$O[(CH$_2$)$_2$O]$_n$(CH$_2$)$_2$—, wherein n is an integer, or a thiaalkylene group, such as —(CH$_2$)$_n$S(CH$_2$)$_m$—, where n and m are each an integer. R in Formulas II and III can be a hydrogen atom or a methyl or ethyl group.

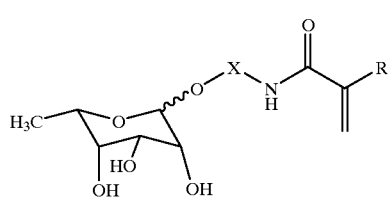
(II)

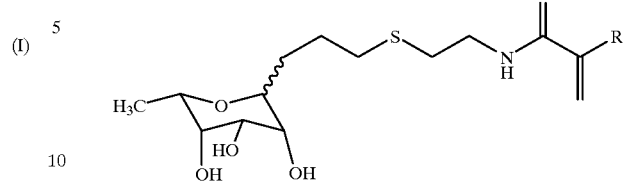
(III)

The invention also comprises fucoside-bearing monomers, wherein the fucoside moiety is attached to the polymerizable unit via a carbon atom bonded directly to the fucoside anomeric carbon atom. Upon polymerization, the monomer can form an addition polymer, for example, when the polymerizable unit is an olefinic bond, or it can form a condensation polymer, for example, when the polymerizable unit is an amino acid or a hydroxy acid.

A preferred polymer of the present invention has the general structure:

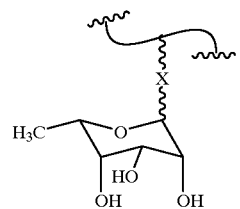

wherein the smooth curve represents the polymer backbone. The fucoside moiety is, preferably, linked to a spacer group (illustrated by a wavy line between X and the smooth curve) at the anomeric carbon via X, which is an oxygen, nitrogen, sulfur or carbon atom. The fucoside moiety can be α- or β-L-fucoside or α- or β-D-fucoside. The spacer group, illustrated by the wavy line between X and the smooth curve, generally has a length ranging from about three to about twelve atoms, which can include, among others, carbon, nitrogen, oxygen and sulfur atoms, and, in a preferred embodiment, terminates in a nitrogen atom which can be, for example, an amide nitrogen of a polyacrylamide backbone. The polymers of the present invention, thus, include homopolymers comprising a monomer of Formula I, Formula II, or Formula III.

The polymer can also be a copolymer comprising a fucoside-bearing monomer, for example a monomer of Formula I, Formula II or Formula III, above, and a second, non-fucoside-bearing monomer, such as underivatized acrylamide. Such a copolymer will preferably comprise a plurality of fucoside-bearing monomers to enable polyvalent binding to the virus surface. In one example of such a copolymer, the composition of the copolymer can vary substantially, ranging from about 5 mole percent to about 50 mole percent of a fucoside-bearing monomer, preferably from about 20 mole percent to about 30 mole percent. The copolymer can, for example, comprise two or more different monomers which are distributed substantially randomly along the polymer chain or can have regions along the polymer chain in which the mole ratio of the monomers is the same as or differs substantially from the mole ratio for the copolymer overall. In another embodiment, the polymer is a copolymer comprising a fucoside-bearing monomer such as a monomer of Formulae I, II and III, and a sialic acid-bearing monomer. Such a copolymer can further comprise a monomer which does not bear a glycoside moiety, such as acrylamide.

Polymers of the present invention also include homopolymers and copolymers comprising a fucoside moiety wherein the fucoside moiety is attached to the polymer backbone via a carbon atom bonded directly to the anomeric carbon atom of the fucoside moiety. Such a polymer can be an addition polymer or a condensation polymer.

Polymer backbones which are suitable for the present invention include backbones with low intrinsic toxicity. For example, the polymer can comprise a polyacrylamide, polyacrylate, polystyrene, poly(vinyl alcohol), poly(vinyl amine) or poly(ethyleneimine) backbone. A co-polymer of the present invention can comprise a combination of two or more backbone elements. For example, the copolymer can be a poly(acrylamide-co-styrene) copolymer wherein the fucoside moiety is attached to either or both of the acrylamide or styrene monomer.

An advantage of the present invention is that fucose is a relatively simple and inexpensive sugar for incorporation into polymers. Previous studies of polymers for the prevention of viral infection have focused on influenza virus and have included the much more expensive sialic acid (N-acetylneuraminic acid) moiety (Sparks et al., *J. Med. Chem.* 36: 778–783 (1993); Spaltenstein et al., *J. Am. Chem. Soc.* 113: 686–687 (1991), Kingery-Wood et al., *J. Am. Chem. Soc.* 114: 7303–7305 (1992); Matrosovich et al., *FEBS Letters* 272: 209–212 (1990); Byramova et al., *J. Carbohydrate Chem.* 10: 691–700 (1991)). Moreover, fucoside-bearing polymers are resistant to neuramidinase, an enzyme found on the surface of influenza virus and other viruses which cleaves sialic acid groups from molecules which approach the virus, thereby destroying the ability of these molecules to bind the virus. Thus flucoside-bearing polymers will maintain activity in vivo longer than sialic acid-bearing polymers.

The present invention also includes the sialic acid-bearing monomers of Formulas IV and V, wherein R is a hydrogen atom or a methyl or ethyl group, as well as polymers and copolymers comprising one of these monomers.

(IV)

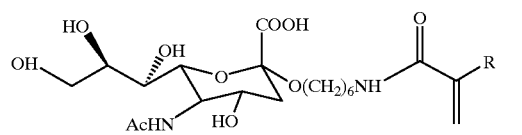

(V)

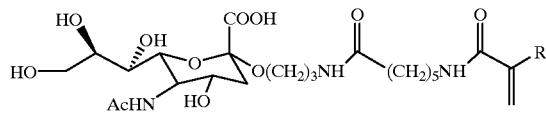

In a preferred embodiment, the polymer comprising the monomer of Formula IV or Formula V is a copolymer further comprising a monomer which does not bear a glycoside moiety, such as acrylamide. The mole percent of the monomer of Formula IV or Formula V in the copolymer can vary substantially, ranging from about 5% to about 50%, preferably from about 20% to about 30%.

In another embodiment, the copolymers of the present invention comprise a glycoside-bearing monomer, a hydrophobic monomer, and, optionally one or more additional monomers. The hydrophobic monomer comprises a hydrophobic moiety, for example, a normal or branched, substituted or unsubstituted $C_3$–$C_{18}$-alkyl group or an aryl or substituted aryl group. Examples of suitable alkyl substituents include halogen atoms, such as fluorine or chlorine atoms and aryl groups, such as a phenyl group. Aryl substituents can include halogen atoms, $C_1$–$C_6$-alkyl groups and $C_1$–$C_6$-alkoxy groups. Suitable hydrophobic monomers include substituted or unsubstituted $C_3$–$C_{18}$-alkylacrylamides, such as N-n-decylacrylamide and N-isopropylacrylamide. Suitable glycoside-bearing monomers include the monomers of Formulas I–V. The additional monomers can be, for example, neutral, hydrophilic monomers, such as acrylamide or N-(2-hydroxyethylacrylamide.

Without being bound by theory, the advantage of polymers comprising both sugar moieties and hydrophobic units lies in their ability to bind to viruses via at least two types of interactions, interactions between the glycoside unit and carbohydrate receptors on the viral surface and interactions between the hydrophobic unit and hydrophobic regions on the viral surface. The presence of hydrophobic units within the polymer could also promote the organization of the polymer into an amphipathic structure comprising discrete hydrophilic and hydrophobic regions, as has been observed for naturally occurring host defense peptides.

The composition of the glycoside-bearing monomer/hydrophobic monomer copolymers can vary substantially. The copolymer can comprise from about 5 to about 50 mole percent, preferably from about 20 to about 35 mole percent, of the glycoside-bearing monomer, and from about 5 to about 50 mole percent, preferably from about 20 to about 35 mole percent, of the hydrophobic monomer.

Examples of the copolymers of the present invention include copolymers comprising a monomer of Formulas I–IV, N-n-decylacrylamide and acrylamide or N-(2-hydroxyethyl)acrylamide. Also included are copolymers comprising a monomer of Formulas I–V with N-isopropylacrylamide and acrylamide or N-(2-hydroxyethyl) acrylamide.

A further embodiment of the present invention includes copolymers comprising at least two different glycoside-bearing monomers. Preferably, the different glycoside-bearing monomers each bear a different glycoside moiety, for example a fucoside, sialic acid or galactosamino moiety. The copolymer can, for example, include a monomer of Formulas I–V, or an aminogalactose-bearing monomer of Formula VI or Formula VII, (VI)

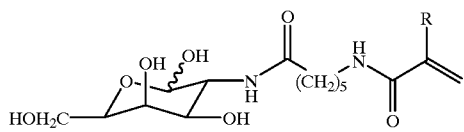

(VII)

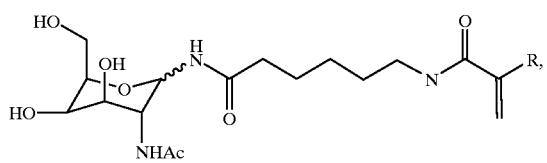

wherein in both formulas R is H, methyl or ethyl. Suitable examples include copolymers comprising a fucoside-bearing monomer and a sialic acid-bearing monomer, copolymers comprising a fucoside-bearing monomer and an aminogalactose-bearing monomer and copolymers comprising a sialic acid-bearing monomer and an aminogalactoside-bearing monomer. Such copolymers can, optionally, include an additional, non-glycoside-bearing monomer, such as a neutral hydrophilic monomer, for example, acrylamide or N-(2-hydroxyethyl)acrylamide. The copolymer can comprise from about 5 to about 50 mole percent, preferably from about 10 to about 35 mole percent, of each glycoside-bearing monomer.

The polymers of the present invention are, preferably, of a molecular weight which enables them to reach and remain in the target region of the body. For example, a polymer which is an agent for inhibiting rotavirus infection should be of sufficiently high molecular weight to resist, partially or completely, absorption from the abdominal tract into other regions of the body, i.e., the polymer should, preferably, remain in the digestive tract. The polymers can have molecular weights ranging from about 2,000 Daltons to about 500,000 Daltons, preferably from about 5,000 Daltons to about 150,000 Daltons.

Without being bound by theory, the presence of two or more different glycoside units pendant from the polymer backbone can enhance binding of the polymer to the virus by enabling the polymer to bind to multiple types of viral carbohydrate receptors. For example, a first viral receptor can be selective for one glycoside unit while a second viral receptor can be selective for another glycoside unit. A polymer containing both glycosides can potentially interact with both receptors simultaneously, increasing the strength of polymer-virus binding.

The polymers of the present invention can be prepared via two general routes, direct polymerization or copolymerization of a fucoside-bearing monomer, and nucleophilic side chain substitution on a activated polymer. A homopolymer comprising pendant fucoside moieties, for example, can be prepared by polymerizing a fucoside-bearing monomer, such as a monomer of Formulae I, II or III. A copolymer comprising pendant fucoside moieties can be prepared by co-polymerizing a fucoside-bearing monomer with a second monomer, such as underivatized acrylamide. The monomers can be polymerized using, for example, methods of free radical polymerization which are well known in the art. Due to reactivity differences between the two monomers, the mole ratio of the monomers in the copolymer product can be different from the mole ratio of the monomers in the initial reaction mixture. This reactivity difference can also result in a non-random distribution of monomers along the polymer chain.

Another synthetic route to polymers comprising pendant fucoside units proceeds via an intermediate polymer having labile side chains which are readily substituted by a desired side chain. Suitable polymers of this type include poly(N-acryloyloxysuccinimide) (pNAS), which reacts with a primary amine, for example, to form an N-substituted polyacrylamide. Another suitable polymer with labile side chains is poly(4-nitrophenylacrylate), which also forms an N-substituted polyacrylamide upon reaction with a primary amine or ammonia.

A co-polymer with a polyacrylamide backbone comprising amide nitrogen atoms substituted with a spacer-glycoside unit and underivatized amide nitrogen atoms can be prepared by treating p(NAS) with less than one equivalent (relative to N-acryloyloxysuccinimide monomer) of a primary amine substituted on nitrogen with a spacer group which terminates in a fucoside moiety. The remaining unreacted N-acryloyloxysuccinimide monomer can then be reacted with ammonia or a second primary amine, to introduce, respectively, underivatized amide groups, or derivatized amide groups with a variety of sizes and polarities. The second amine, for example, can comprise a glycoside moiety, or a hydrophobic or hydrophilic N-substituent. A co-polymer comprising more than two types of acrylamide monomers can be prepared by reacting the activated polymer with three or more primary amines or ammonia. A variety of copolymer compositions can, thus, be readily obtained by treating the activated polymer with different ratios of the amines.

Another embodiment of the present invention is a method for treating a rotavirus infection in a mammal, for example, a human, comprising administering to the mammal a therapeutically effective amount of a polymer comprising one or more glycoside moieties, such as pendant glycoside moieties. As used herein, a "therapeutically effective amount" is an amount sufficient to inhibit or prevent (partially or totally) a viral infection or to reverse development of a viral infection or prevent or reduce its further progression.

In one embodiment, the polymer to be administered comprises one or more pendant fucoside moieties. This polymer is, preferably, a polymer of the present invention, as described in detail above. Thus, in a particularly preferred embodiment, the polymer comprises a monomer of Formulae I, II, or III. The polymer can also be a copolymer comprising one of these monomers as well as a monomer which does not bear a glycoside moiety, such as acrylamide.

The polymer to be administered can also comprise a fucoside-bearing monomer, wherein the fucoside moiety is connected to the polymerizable unit of the monomer via a carbon atom directly bonded to the anomeric carbon of the fucoside moiety. Such a polymer can be a homopolymer or a copolymer, and can further be an addition polymer or a condensation polymer.

In another embodiment of the method, the polymer to be administered comprises a sialic acid moiety, such as a pendant sialic acid moiety. In one embodiment, the sialic acid moiety is linked to the polymer backbone by a spacer group, such as a straight chain or branched alkylene group, or an alkylene group wherein one or more carbon atoms are substituted by heteroatoms. A preferred polymer for use in the present method comprises the monomer of Formula IV, above. In a particularly preferred embodiment, the polymer is a copolymer comprising the monomer of Formula IV and a second monomer, such as acrylamide.

Several polymers bearing pendant sialic acid moieties have been described in the literature (Sparks et al., supra (1993); Spaltenstein et al., supra (1991), Kingery-Wood et al., supra (1992); Matrosovich et al., supra (1990); Byramova et al., supra (1991)). Those which are suitable for use in the present method include polymers or copolymers comprising a monomer of Formula V (Sparks et al., supra (1993), wherein R can be a hydrogen atom or a methyl or ethyl group. In one embodiment of the method, the polymer to be administered is a copolymer comprising a monomer of Formula V, a fucoside-bearing monomer, such as a monomer of Formula I, Formula II or Formula III, and, optionally, a monomer which does not bear a glycoside moiety. The copolymer can also comprise a monomer of Formula VIII, wherein R is a hydrogen atom or a methyl or ethyl group, and a monomer which does not bear a glycoside moiety, such as acrylamide, N-(2-hydroxyethyl)acrylamide, or (2-hydroxyethyl)vinylamine.

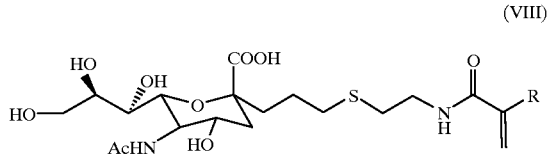

(VIII)

In another embodiment, the polymer to be administered comprises a glycoside moiety and a hydrophobic group preferably, the polymer is a copolymer comprising a glycoside-bearing monomer and a hydrophobic monomer. Suitable glycoside-bearing monomers include the monomers of Formulas I–VIII. The hydrophobic monomer can comprise a hydrophobic moiety such as a $C_3$–$C_{18}$-alkyl group or an aryl group. The copolymer can further comprise an additional monomer, such as a neutral hydrophilic monomer. Copolymers of this type which are of use in the present method include the glycoside-bearing monomer/hydrophobic monomer copolymers described above.

The polymer to be administered can also be a copolymer which comprises a first glycoside moiety and one or more additional glycoside moieties which are structurally distinct from the first glycoside moiety. Preferably, the polymer is a copolymer comprising at least two different glycoside-bearing monomers. Such a copolymer, for example, can comprise a fucoside-bearing monomer and a sialic acid-bearing monomer, a fucoside-bearing monomer and a aminogalactoside-bearing monomer or a sialic acid-bearing monomer and an amino-galactoside-bearing monomer. Copolymers of this type which are of use in the present method include those discussed above.

The polymer can be administered orally, rectally or by any additional means which can deliver the polymer to the intestinal tract. The quantity of an individual polymer to be administered will be determined on an individual basis and will be determined, at least in part, by consideration of the individual's size, the severity of symptoms to be treated and the result sought. The polymer can be administered as a solid or in solution, for example, in aqueous or buffered aqueous solution. The polymer can be administered alone or in a pharmaceutical composition comprising the polymer, an acceptable carrier or diluent and, optionally, one or more additional drugs.

Several polymers of the present invention have been tested in the suckling mouse model for efficacy in inhibiting rotavirus infection. As described in Example 20, each mouse was inoculated with 5 μL of a virus preparation. On the first day post-infection, each mouse was treated three times a day with 5 μL of polymer solution; the control mice were treated with 5 μL water. The polymer concentration in the polymer solutions ranged from 5% to 20% by weight. The activity of each polymer was determined by comparing intestinal virus levels of polymer-treated mice and control mice. The activity of the polymer was then expressed as the percent reduction in virus level in the polymer-treated mice relative to the control mice.

The results of these studies are summarized in the Table included in Example 20. The polymers tested are defined in the examples. Three polymers tested, 16a, 16b, and 18b, showed minimal or no activity at a concentration of 5%. The activity of 16b, however, increases to 6–20% at a concentration of 20%. Three other polymers, 18a, 23, and 32, show a high degree of activity, 76–100%, when administered at concentrations ranging from 5–10% by weight.

The invention will now be further and specifically described by the following examples.

EXAMPLES

Example 1

Preparation of N-Carbobenzyloxy-6-Aminohexan-1-ol, 4

6-Aminohexan-1-ol (11.7 g, 100 mmol) and potassium carbonate (16.58 g, 120 mmol) were dissolved in 100 mL water and 70 mL dichloromethane. Benzylchloroformate (14.27 mL, 100 mmol) was added dropwise over 30 minutes at a temperature of 25–30° C. The resulting mixture stood overnight, then the dichloromethane layer was separated, washed with water (3×200 mL), 2 N HCl (3×50 mL) and finally with water (3×100 mL), dried, and evaporated to give a white solid. The solid was recrystallized in hexane-ethylacetate (8:2) to give a solid, which was collected and dried under vacuum at room temperature. Yield: 23 g (91%).

Example 2

Preparation of 8-Azido-3,6-Dioxa-1-Octanol, 5

Triethylene glycol (19.42 g, 100 mmol) was converted to the monotosylate by reaction with tosylchloride (4.76 g, 25 mmol) in dichloromethane (200 mL) containing triethylarnine (6.95 g, 50 mmol) and catalytic 4-(N,N-dimethylamino)pyridine (1 mmol) at room temperature for 24 h. The dichloromethane and triethylamine were removed under vacuum to give a semi-solid. This material was partially dissolved in 250 mL of ethylacetate and the insoluble triethylamine hydrochloride was removed by filtration. The filtrate was washed with 2×20 mL of 2 N HCl, 3×20 mL of saturated $NaHCO_3$ and finally with 2×20 mL of saturated NaCl solution. The organic layer was dried over sodium sulfate and the solvent removed to give a gum (7.2 g; 79% yield based on tosyl chloride). IR: 3400 cm$^{-1}$, OH stretch. $^1$H NMR (CDCl$_3$, ppm) δ 8.0–7.9 d and 7.7–7.6 d, 4H, tosyl ring protons; 4,2, m, 2H; 3.8–3.6, m, 14H (several CH$_2$s); 2.6, s, 3H (tosyl methyl protons).

The monotosylate (5.0 g, 16.4 mmol) and sodium azide (2.9 g, 45 mmol) were dissolved in 200 mL of 50% aqueous methanol and stirred at 60° C. for 48 h. The methanol was removed under vacuum and partitioned with dichloromethane. The dichloromethane layer was collected and washed with water, dried and evaporated. The azide was obtained as a colorless liquid, 2.5 g (72% yield) which was analyzed by IR and GC. IR: 3400 cm$^{-1}$ (OH stretch) and 2098 cm$^{-1}$ (azide stretch). This material was used directly in coupling.

Example 3

Preparation of 11-Azido-3,6,9-Trioxa-1-Undecanol, 6

This compound was prepared from tetraethyleneglycol via the corresponding tosylate as described above for the preparation of 5 in Example 2. This material was used directly in coupling.

Example 4

Preparation of Polymer Bound L-Fucose, 16a
Preparation of 1,2,3,4 tetra-O-acetyl-α-L-fucose, 2a To 35 mL of acetic anhydride and 0.25 mL of 60% perchloric acid in a round bottom flask, 5.0 g of L-fucose were added slowly with stirring over a period of 30 minutes, keeping the reaction temperature between 30 and 40° C.

Stirring was continued for 30 min after the addition was complete. The mixture was poured into ice-water and extracted with dichloromethane (100 mL). The extract was immediately poured into ice/saturated sodium bicarbonate solution and stirred for 5 minutes, then the dichloromethane layer was separated, washed with water, dried over sodium sulfate, and evaporated to give a colorless viscous gum. The gum was dissolved in anhydrous ether, and hexane was added dropwise until the solution became opaque. Then mixture was then stored in a refrigerator overnight. The white crystals were isolated by filtration and dried in a vacuum oven at room temperature (7.4 g, 76% yield). $^1$H NMR (CDCl$_3$, ppm) δ 1.154 d, 3H, CH$_3$; 2.0, 2.019, 2.15, 2.18, 4s, 12H, CH$_3$COO—; 4.286, m, 1H, H-5; 5.34, s, 3H, H-2, H-3, H-4; 6.43, d, 1H, H-1: $^{13}$C NMR (CDCl$_3$) δ 15.99(C-6); 20.69, 20.74 and 20.989 (4C, CH3COO—); 66.4(C-2); 67.23(C-5); 67.76(C-3); 70.51(C-4); 89.88 (C-1); 168.96, 169.77, 170.02, 170.34 (4C, CH3COO).

Preparation of 1-bromo-2,3,4-tetra-O-acetyl-L-fucose, 3a 1,2,3,4-tetra-O-acetyl-L-fucose, 2, (2 g) was dissolved in 20 mL dichloromethane and cooled to 0° C., then 1.5 mL 30% HBr in acetic acid was added via syringe. After storage at 0° C. for 4 h, the solution was diluted with 50 mL of dichloromethane and poured into ice/saturated sodium bicarbonate solution. The dicloromethane layer was collected, washed with water, dried and evaporated to give a colorless gum (1.9 g). The freshly prepared bromo derivative 3a was used directly to couple the spacers without further purification or characterization.

Preparation of 1-(N-carbobenzyloxy-6-aminohexyl)-2,3,4-triacetyl-L-fucose, 7a

The 2,3,4-triacetyl-L-fucosyl bromide 3a (1.9 g, 6 mmol) was coupled to N-carbobenzoyloxy-6-amino-1-hexanol 4a (2.0 g, 6 mmol) using silver salicylate (4 g) in CH$_2$Cl$_2$ (30 mL) and 4A molecular sieves at room temperature under dark for 72 h. The reaction mixture was filtered and washed with 30 mL of dichloromethane. The filtrate was washed with 10% sodium thiosulfate solution (2×20 mL) followed by saturated sodium bicarbonate solution (2×20 mL) and water (2×30 mL). The dichloromethane layer was dried over anhydrous sodium sulfate and the solvent was removed under vacuum at room temperature. The crude glycoside was obtained as a brown gum. The protected glycoside was purified on a silica gel column using hexade-ethylacetate (1:3) as the eluant. The glycoside 7a was obtained as a clear colorless gum (2.1 g, 66% yield).

Preparation of 1-O-(6-aminohexyl)-L-fucose, 10a

The glycoside derivative 7a was de-acetylated with sodium methoxide in methanol, then subjected to hydrogenolysis to give the free amine. The free amine was purified on a silica gel column with 15% methanol in dichloromethane as eluant. Appropriate fractions (judged by TLC) were pooled and evaporated to give a gum (700 mg, 67% yield).

Preparation of 1-O-(N-acryloyl-6-aminohexyl)-L-fucose, 13a

The free base 10a was converted to a polymerizable acrylamide derivative by treatment with acryloyl chloride at pH 10.5. After purification on a silica gel column using 20% methanol in dichloromethane, pure acrylamide monomer (480 mg, 57% yield) and some contaminated derivative (200 mg) were isolated. The pure fraction was used in the next reaction.

Preparation of acrylamide copolymer 16a

Monomer 13a (300 mg) and acrylamide (217 mg) were dissolved in water and purged with nitrogen for 5 minutes, then initiator (V-50) was added. The solution was heated in a hot water bath to 60° C. for 30 minutes. The solution became viscous at 55° C. and was removed from the heat and stirred for 24 hours. The viscous solution was then added dropwise to isopropanol with stirring, precipitating the polymer as a white powder which was collected by filtration. The powder was dried under vacuum at room temperature to give (479 mg) of polymer as a white powder. The polymer forms a homogeneous solution in water.

Example 5

Preparation of Polymer Bound L-Fucose, 17a
Preparation of 1-O-(8-azido-3,6-dioxaoctyl)-2,3,4-triacetyl-L-fucose, 8a The 2,3,4-triacetyl-L-fucosyl bromide 2a (1.9 g, 6 mmol) was coupled to the 8-azido-3,6-dioxa-1-octanol (2.0 g, 6 mmol) as described for the preparation of 7a in Example 4. The protected glycoside was purified on a silica gel column using dichloromethane:methanol (98:2) as eluant. The glycoside was obtained as a colorless gum (1.4 g, 50% yield).

Preparation of 1-(8-amino-3,6-dioxaoctyl)-L-fucose, 11a

The glycoside derivative 8a (1.4 g) was de-O-acetylated with sodium methoxide in methanol, then subjected to hydrogenolysis. The resulting free base was purified on a silica gel column with 15% methanol in dichloromethane as eluant to give pure 11a as a gum (700 mg, 76%).

Preparation of 1-(8-acrylamido-3,6-dioxaoctyl)-L-fucose, 14a

The free base (700 mg) was converted to polymerizable acrylamide derivative by treating with acryloyl chloride at pH 10. After purification on a silica gel column using 12% methanol in dichloromethane as eluent, pure acrylamide monomer (300 mg, 42%) and some contaminated monomer (200 mg, 27%) were isolated.

Preparation of Polymer 17a

Pure monomer 14a (300 mg) and acrylamide (217 mg) were polymerized by the method described for the preparation of polymer 16a in Example 4, yielding 470 mg of polymer as a white powder.

Example 6

Preparation of the Polymer Bound L-Fucose 18a
Preparation of 11-azido-3,6,9-trioxaoctyl-2,3,4-triacetyl-L-fucose, 9a This compound was prepared from 2,3,4-tricetyl-D-fucosyl bromide and 11-azido-3,6,9-trioxa-1-octanol in 50% yield as described for the synthesis of 8a in Example 5.

Preparation of 1-(11-amino-3,6,9-trioxaoctyl)-L-fucose, 12a

This compound was prepared from 9a in 75% yield by the method described in Example 5 for the preparation of 11a.

Preparation of 1-(11-acrylamido-3,6,9-trioxaoctyl)-L-fucose, 15

This monomer was prepared from 12 in 50% yield by the method described for the synthesis of 14 in Example 5.

Preparation of Polymer 18a

Monomer 15 (300 mg) and acrylamide (217 mg) were polymerized as described for the preparation of polymer 16a in Example 4 to give 450 mg of polymer.

Example 7

The Preparation of Polymer Bound D-Fucose Derivatives 16b–18b

The O-linked D-fucose acrylamide copolymers containing 6-amino-1-hexanol, 8-amino-3,6-dioxa-1-octanol and 11-amino-3,6,9-trioxa-1-undecanol spacers were prepared by the method described for the synthesis of polymer 16a in Example 4.

Example 8

Preparation of Polymer Bound C-Linked Fucose, 23

Preparation of 1-C-α-allyl-2,3,4-tri-O-acetyl-L-fucoside, 19

Tetraacetyl-L-fucose 2 (1.0 g) was treated with allyltrimethylsilane (1 g) and boron trifluoride-etherate (0.4 mL) in acetonitrile (20 mL) at 20° C. After 24 h, the reaction was quenched with sodium bicarbonate solution, then extracted with diethyl ether, dried, evaporated, to give a gum (1.1 g). This was purified by chromatography on silica gel and gave pure α isomer (1.0 g) and β isomer (0.1 g). $^1$H NMR (CDCl$_3$) of α isomer: δ 1.14, d, 3H; 2.015, s, 3H; 2.15, s, 3H; 2.24–2.34, m, 1H; 5.31, dd, 10 Hz, 1H; 5.73–5.82, m, 1H; $^{13}$C NMR (CDCl$_3$): δ 15.8, 20.50, 20.61, 20.70, 30.46, 65.46, 68.05, 68.40, 70.55, 71,84, 117.22, 133.72, 169.8, 170.10, 170.44.

Preparation of 1-C-α-allyl-L-fucose, 20

Compound 19 was saponified with sodium hydroxide solution, acidified and evaporated to give a gum. This gum was purified on silica gel using 5 to 15% methanol in dichloromethane. The compound was obtained as a white solid, 500 mg.

Preparation of 1-C-α-(6-amino-4-thiahexyl)-L-fucoside, Hydrochloride Salt, 21

Compound 20 (500 mg, 3 mmol) was coupled to aminoethanethiol HCl (680 mg, 6 mmol) in water under UV irradiation with 10 mg of azobisisocyanovaleric acid AlCV) as an initiator. The resulting crude mixture was purified on a Biogel P2 size exclusion chromatography column, using water as an eluant. Appropriate fractions were pooled and evaporated under vacuum to give a gum (718 mg; 92% yield).

Preparation of N-(6-(1-C-α-fucosyl)-3-thiahexyl)-acrylamide, 22

The free base 21 (718 mg, 2.9 mmol) was converted to polymerizable acrylamide derivative 22 by treatment with N-acryloyloxysuccinimide (1.0 g, 5 mmol) in 3 mL water-methanol (1:1) and 1 mL triethylamine. The monomer was purified on a silica gel column to give 486 mg (55% yield) of pure monomer 22 as a white solid and an impure fraction (190 mg). The pure compound was used in polymer preparation.

Preparation of Polymer 23

Monomer 22 (460 mg, 1.44 mmol) and acrylamide (511 mg, 7.21 mmol) were dissolved in 4 mL of pure water and the solution was purged with nitrogen. Then, 5 mg of V-50 initiator was added and the solution was heated to 60° C. The solution became viscous within 30 minutes and heating was stopped. After 24 h, the viscous solution was added to isopropanol dropwise. The polymer was precipitated as a white mass which was filtered and dried in vacuum at room temperature for 48 h. The polymer was obtained as a white solid (640 mg) in 66% yield.

Example 9

The Preparation of O-Linked Sialic Acid Bound Polymer 32

Preparation of Sialic Acid Methyl Ester, 25

A mixture of 3.0 g of sialic acid 24 and 16.6 g of Dowex W50 (H+) resin in 335 mL methanol was stirred at room temperature for 3 h. The undissolved sialic acid slowly disappeared during the course of reaction. The resulting homogeneous solution was decanted and stored in the refrigerator. Methanol (235 mL) was added to the resin and stirring continued for 2 h at room temperature. The solution was then decanted and the resin was washed with an additional 400 mL methanol. The combined decants were evaporated under vacuum to give 4.1 g of the methyl ester as a white solid (95% yield). TLC: methanol/dichloromethane (1:3), Rf 0.32, produced brown to black spot (10% H$_2$SO$_4$, heat). $^1$H NMR (60MHz, D$_2$O): δ 2.1, s, 3H, N—COCH$_3$; 3.8, s, 3H, —COOMe: 3.4–3.7, m, and 3.854.0, m, 9H.

Preparation of methyl 5-acetamido-4,7,8,9-tetra-O-acetyl-2-chloro-3,5-dideoxy-D-glycero-D-galacto-α-nonulopyranosoate, 26:

The methyl ester derivative 25 (4.0 g) was dissolved in 300 mL acetyl chloride in a 1 L round bottom flask, stoppered and stirred at room temperature for 24 h. The resulting homogeneous solution was evaporated under vacuum and coevaporated with chloroform (5×50 mL) to yield the crude halide 26 as a white foam. $^1$H NMR (CDCl$_3$): δ 2.0–2.3, m, 15H, N-acetyl and O-acetyl groups; 3.9, s, 3H, —COOCH$_3$; 3.5–3.9, m, 5H; 3.8–4.0, m, 4H.

Preparation of methyl 5-acetamido-4,7,8,9-tetra-O-acetyl-2-O-(N-carbobenzyloxy-6-aminohexyl)-3,5-dideoxy-D-glycero-D-galacto-α-nonulopyranosoate, 27

The chloro derivative 26 was dissolved in 40 mL of anhydrous dichloromethane, to which 4A molecular sieves (4 g), Cbz protected aminohexanol (9 g) and silver salicylate (13 g) were added, and the resulting mixture was stirred in the dark for 4 days at room temperature. The silver chloride was filtered, the filtrate was washed with 10% sodium thiosulfate (3×35 mL), then with saturated sodium bicarbonate (3×30 mL) and finally with water (3×100 mL). The dichloromethane layer was dried over sodium sulfate and evaporated under vacuum to give a brown solid. This was used directly in the next step without purification.

Preparation of methyl 5-acetamido-2-O-(N-carbobenzyloxy-6-aminohexyl)-3,5-dideoxy-D-glycero-D-galacto-α-nonulopyranosoate 28

The crude solid 27 obtained as described above was dissolved in 50 mL methanol, and freshly prepared sodium methoxide was added to achieve pH1 11.5. The resulting mixture was stirred at room temperature for two days. During this period, the pH was monitored several times and adjusted to 11.5 with sodium methoxide solution. When the pH stabilized, indicating completion of deprotection (confirmed by TLC, methanol/dichloromethane 3:1, Rf=0.60, dark-brown to black spot produced with sulfuric acid spray on heating), the reaction was acidified with Dowex-H type resin to pH 2.0, filtered and evaporated to obtain a brown solid. The solid was partitioned between 50 mL of water and 50 mL of ethyl acetate. The water layer was separated and extracted with 2×50 mL ethyl acetate and the combined ethyl acetate extracts dried over sodium sulfate and evaporated to give a white solid. The solid was purified by chromatography on silica gel with a gradient from ethyl acetate to 10% methanol in ethyl acetate as eluant. The appropriate fractions, as judged by TLC analysis, were pooled and evaporated under vacuum to give 28, 1.0 g (20% yield over four steps) of pure methyl ester of N-CBz aminohexylsialoside as a white foam. $^1$H NMR (CD$_3$OD): δ 1.4–1.8, m, 10H; 2.1–2.2, s, 3H, N-acetyl; 3.1–3.4, m, 2H; 3.8–3.9, m, 9H; 3.95–4.0, s, 3H, —COOMe; 4.9, s, 2H, C$_6$H$_5$CH$_2$: 7.2–7.4, s, 5H,C$_6$H$_5$CH2:

Preparation of 5-acetamido-2-O-(N-carbobenzyloxy-6-aminohexyl)-3,5-dideoxy-D-glycero-D-galacto-α-nonulopyranosoate, 29

The derivative 28 (1.0 g), obtained as described above, was saponified with 2M NaOH in water at room temperature at pH 11.5. At the completion of the reaction, the mixture was acidified with Dowex-H type resin to pH 2.0, filtered and evaporated to give 900 mg of pure N-CBz-aminohexyl sialoside 29 as a pale yellow foam. $^1$HNMR(CD$_3$OD): δ 1.4–1.8, m, 10H; 2.1–2.2, s, 3H, N-acetyl; 3.1–3.4, m, 2H; 3.8–3.9, m, 9H; 4.9, s, 2H, C$_6$H$_5$CH$_2$; 7.2–7.4, s, 5H, C$_6$H$_5$CH$_2$:

Preparation of 5-acetamido-2-O-(6-aminohexyl)-3,5-dideoxy-D-glycero-D-galacto-α-nonulopyranosoate 30

The intermediate 29 (900 mg), obtained as described above, was subjected to hydrogenolysis in methanol (50 mL) using 10% Pd/charcoal (500 mg) at 50 psig for 6 h. The charcoal was filtered and washed with 100 mL of methanol, the combined methanol solution was evaporated under vacuum at room temperature to give 740 mg of pure minohexyl sialoside as a white foam. $^1$H NMR (CD$_3$OD): δ 1.4–1.8, m, 10H; 2.1–2.2, s, 3H, N-acetyl; 3.1–3.4, m, 2H; 3.8–3.9, m, 9H.

Preparation of 5-acetamido-2-O-(N-acryloyl-6-aminohexyl)-3,5-dideoxy-D-glycero-D-galacto-α-nonulopyranosoate 31

The free base 30 (720 mg, 1.91 mmol) was dissolved in 5 mL 2M NaOH and treated with 345 mg (3.8 mmol) acryloyl chloride for 5 h at room temperature. TLC analysis (methanoldichloromethane 1:3, Rf of product=0.40, Rf of free base=0.15) indicated the completion of reaction. The reaction mixture was acidified with Dowex-H+ type resin to pH 2.0, then the resin was filtered. The filtrate was evaporated under vacuum at room temperature to give a viscous gum. This was purified on a silica gel column with 10% methanol in dichloromethane as the initial eluant and then with butanol: acetic acid: water (5:4:1). The product was eluted in the butanol-acetic acid-water fraction. The solvent was removed from this fraction under vacuum at 35° C. to give a gum. This was further purified on an ion exchange (AG 1X8, formate form) column with 0 to 1 M formic acid in water as a gradient. The product was eluted at an eluent composition of 0.5 M HCOOH, as judged by TLC. Appropriate fractions were pooled, and water was removed to give pure monomer 31 (187 mg, 25%) as a white foam. Some monomer contaminated with unreacted free base was also obtained. $^1$H NMR (CD$_3$OD); δ 1.4–1.8, m, 10H; 2.1–2.2, s, 3H, N-acetyl; 3.1–3.4, m, 2H; 3.8–3.0, m, 9H; 5.8–6.0, m, 1H; 6.2–6.4, m, 2H.

Preparation of Acrylamide-Sialic Acid Copolymer 32

Monomer 31 (187 mg, 0.42 mmol), acrylamide (120 mg, 1.69 mmol) and 2 mg of V-50 initiator were dissolved in 2 mL water and heated in a water bath to 65° C. while stirring and purging with nitrogen. The solution became viscous at 60° C., and was removed from the heat. Stirring and nitrogen purging continued over night. The viscous solution was added dropwise to isopropanol while stirring. This precipitated a white solid, which was washed with fresh isopropanol (3×10 mL) and dried under vacuum at 40° C. to give 266 mg of polymer 32 as a white powder.

Example 10

Preparation of Fucose-n-Decyl Acrylamide Copolymer 33

A solution was prepared of poly(N-acryloyloxysuccinimide)(pNAS; 1.5 g, 8.87 mmol) in dimethylformamide (DMF, 60 mL). To this solution was added triethylamine (1.5 mL), followed by the dropwise addition of the L-fucose derivative 1 (667 mg, 2.21 mmol, 25 mol % with respect to pNAS). The solution was stirred at room temperature for 12 h, and subsequently heated to 40° C. for 24 h. The solution was cooled and n-decylamine (138 mg, 20 mol % with respect to pNAS) was added as a solution in DMF (1 mL). The solution was stirred at 40° C. for a further 24 h, followed by the addition of ethanolamine (2 mL, excess as a solution in 5 mL of DMF). The reaction mixture was stirred for 243 h at 40° C., cooled and precipitated into acetone (300 mL). The polymer was recovered by centrifugation, washed with acetone (10 mL) and the finely divided white solid dissolved in deionized water (10 mL) and dialysed against water for 24 h. The clear solution was lyophilized to dryness to give the desired product in 72% yield.

Example 11

Preparation of Sialic Acid-n-Decyl Copolymer 39
Preparation of Methyl 5-acetamido-4,7,8,9-tetra-O-acetyl-2-(O-3-azidopropyl)-3,5-dideoxy-D-glycero-D-galacto-α-nonulo-pyranosoate, 34

Methyl 5-acetamido-4,7,8,9-tetra-O-acetyl-2-chloro-3,5-dideoxy-D-glycero-D-galacto-α-nonulo-pyranosoate 26 (30 g) and 12 g of silver salicylate were dissolved in 70 g of 3-azidopropan-1-ol and stirred for 24 h at room temperature. The reaction mixture was partitioned between water (200 mL) and dichloromethane(200 mL). The dichloromethane layer was collected and washed with 10% sodium thiosulfate solution (2×100 mL). Drying over sodium sulfate and evaporation of the solvent gave a light brown syrup which was purified on silica gel column using 20% ethyl acetate in hexane as an eluant. The product was obtained as an oil (22 g). $^1$H NMR (CDCl3): d 1.24–1.28, t, 2H; 1.886, s, 3H; 1.93–1.94, m, 1H; 2.021, s, 3H; 2.12–2.14, m, 2H; 2.18–2.19, d, 6H; 2.59–2.61,dd, 1H; 3.38–3.40,t, 2H; 3.87, s, 3H; 4.113–4.15,m,3H; 4.32–4.33,dd, 1H; 4.8,m, 1H; 5.2–5.31,m,1H; 5.6–5.8,m,2H; 5.52–5.58,m,2H; 6.01,d, 1H: $^{13}$C NMR in (CDCl3): 170.819 (COOMe); 170.52 (NHCOCH3); 170.050(OCOCH3); 169.97 (OCOCH3); 169.87(OCOCH3); 168.16(OCOCH3); 98.58 (C-2 a—linkage); 72.412 (C-6); 68.97, (C-7); 68.30(C-8); 67.19 (C-4); 62.37 (C-9); 61.57 (C of spacer); 52.87 (COOCH3); 49.36, (C-5); 48.09 (C of spacer); 38.0, C-3; 29.02, (C of spacer); 23.25, (NHCOCH$_3$); 20.8, 20.52, 20.51, 20.50 (OCOCH$_3$); IR (neat, film): 2099 cm$^{-1}$ (N$_3$ band).

Preparation of Methyl 5-acetamido-4,7,8,9-tetra-O-acetyl-2-(O-3-aminopropyl)-3,5-dideoxy-D-glycero-D-galacto-a-nonulopyranosoate, 35

The azide derivative 34 (22 g) was subjected to hydrogenolysis in methanol using 10% Pd/charcoal (3.0 g) under hydrogen at 40 psig for 6 h. The charcoal was removed by filtration and the filtrate was evaporated to give a foam (20 g). The absence of a band at 2099 cm$^{-1}$ in the IR spectrum revealed that the azide functionality was converted to amine. This result was confirmed by a positive ninhydrin reaction.
Preparation of Methyl 5-acetamido-4,7,8,9-tetra-O-acetyl 2-O-[3-(N-CBz-aminohexanoyl)propyl)-3,5-dideoxy-D-glycero-D-galacto-a-nonulopyranosoate, 36

Methyl 5-acetamido-4,7,8,9-tetra-O-acetyl-2-(O-3-aminopropyl)-3,5-dideoxy-D-glycero-D-galacto-a-nonulopyranosoate 35 (20 g) was dissolved in dioxane (100ml), to which N-(6-N-Cbz-hexanoyl)oxysuccinimide (18 g) was added followed by 6 mL of triethylamine. The reaction mixture was stirred for 18 h at room temperature. The dioxane was removed, the residue was dissolved in dichloromethane and washed with water (2×100 mL), 2N HCl (2×50 mL) and finally with water (2×100 mL). The dichloromethane layer was dried over sodium sulfate and the solvent was removed under vacuum. The residue was chromatographed on silica gel column with 80% EtOAc in hexane. The pure fraction was collected as a colorless gum (13 g). Another fraction (10 g) which was slightly contaminated was also collected. The pure fraction was used in the subsequent reactions. $^1$H NMR (CDCl3): d1.3–1.4, m, 2H; 1.48–1.56, m, 2H; 1.62–1.7, m, 2H; 1.72–1.78,m,2H; 1.88,s, 3H; 1.90–1.91,m, 1H; 2.02–2.03,s, 9H; 2.07–2.09,m,6H; 2.51–2.54,dd,1H; 3.181–3.191,m, 2H; 3.31–3.33, m,2H; 3.7–3.72,m,2H; 3.77,s, 3H; 4.06–4.10,m, 3H; 4.30–4.32,dd, 1H; 4.82–4.84,m,2H; 5.08,s,2H (CH2C6H5); 5.34–5.35,m, 2H; 6.2–6.21, m, 1H; 7.33–7.34,s, 5H, (CH2C6H5): $^{13}$C NMR in (CDCl3): 172.6, 170.86, 170.78, 170.15, 170.13, 169.911, 168.10, 156.24, 136.44, 128.30, 127.90, 116.36, 98.64 (C-2 a-linkage); 72.338, 68.88, 68.58, 68.15, 67.10, 66.48, 63.56, 62.61, 62.40, 52.88, 49.32, 44.31, 40.84, 38.01, 36.84, 36.40, 29.69, 29.22, 26.40, 25.30, 23.23, 21.25, 20.90

Preparation of 5-acetamido-2-O-[3-(6-N-CBz-aminohexanoyl) propyl)-3,5-dideoxy-D-glycero-D-galacto-a-nonulopyranosonic acid, 37

Methyl 5-acetamido-4,7,8,9-tetra-O-acetyl-2-O-[3-(N-CBz-aminohexanoyl)propyl)-3,5-dideoxy-D-glycero-D-galacto-a-nonulopyranosoate, 36, (12 g) was treated with 1M NaOH in water at room temperature. After the reaction was complete (judged by TLC), the reaction mixture was acidified with Dowex (H$^+$) resin. The resin was removed by filtration, the filtrate was lyophilized to give a white powder (7.8 g). The $^1$H indicated the absence of O-acetyl protons and methyl ester peaks. The remaining spectral characteristics were the same as the above derivative.

Preparation of 5-acetamido-2-O-[3-(6-aminohexanoyl) propyl)-3,5-dideoxy-D-glycero-D-galacto-a-nonulopyranosonic acid, 38

5-Acetamido-2-O-[3-(N-CBz-aminohexanoyl)-propyl)-3,5-dideoxy-D-glycero-D-galacto-a-nonulopyranosonic acid 37 (7–8 g) was subjected to hydrogenolysis in methanol using 10% Pd/C (2.0 g) under hydrogen at 50 psi for 6 h. The charcoal was removed by filtration, the solvent was removed under vacuum to give the free base as a white foam (6.3 g). 1H NMR spectrum showed absence of peaks at 7.3 and 5.08 ppm indicating that the benzyloxycarbony group was cleaved.

Preparation of Polymer 39

A solution was prepared of pNAS (1.0 g, 5.91 mmol) in dimethylformamide (DMF, 50 mL). To this solution was added triethylamine (1.0 mL), followed by the dropwise addition of the tailed sialic acid derivative 38 (526 mg, 1.18 mmol, 20 mol % with respect to pNAS). The solution was stirred at room temperature for 16 h, and subsequently heated to 40° C. for 18 h. The solution was cooled and n-decylamine (138 mg, 20 mol % with respect to pNAS) was added as a solution in DMF (1 mL). The solution was stirred at 40° C. for a further 24 h, followed by the addition of ethanolamine (2 mL, excess as a solution in 5 mL of DMF). The reaction mixture was stirred for 24 h at 40° C., cooled, poured into a dialysis bag (MW cut-off 12,000–14,000), dialysed against water for 24 h. The clear solution was lyophilized to dryness to give the desired product in 72% yield.

Example 12

Preparation of Fucose-n-Decyl Acrylamide Copolymer 40

To a solution of pNAS (1.0 g, 5.91 mmol) in dimethylformamide (DMF, 50 mL) was added triethylamine (1.0 mL), followed by the dropwise addition of the L-fucose derivative 22 (356 mg, 1.18 mmol, 20 mol % with respect to pNAS). The solution was stirred at room temperature for 16 h, and subsequently heated to 40° C. for 18 h. The solution was cooled and n-decylamine (233 mg, 25 mol % with respect to pNAS) was added as a solution in DMF (1 mL). The clear solution was stirred at room temperature for 12 h, followed by dialysis against water using dialysis tubing with a cut-off of 12,000–14,000 kD. The product was recovered by lyophilization. Yield 74%.

Example 13

Preparation of Fucose-Isopropyl Acrylamide Copolymer 41

To a solution of pNAS (1.0 g, 5.91 mmol) in dimethylformamide (DMF, 50 mL) was added triethylamine (1.0 mL), followed by the dropwise addition of the L-fucose derivative 22 (356 mg, 1.18 mmol, 20 mol % with respect to pNAS). The solution was stirred at room temperature for 16 h, and subsequently heated to 40° C. for 18 h. The solution was cooled and isopropylamine (233 mg, 25 mol % with respect to pNAS) was added as a solution in DMF (1 mL). The solution was stirred at 40° C. for a further 24 h, cooled and added to a solution of conc. NH$_4$OH (20 mL). The clear solution was stirred at room temperature for 12 h, followed by dialysis against water using dialysis tubing with a cut-off of 12,000–14,000 kD. The product was recovered by lyophilization. Yield 82%.

Example 14

Preparation of Fucose-Isopropyl Acrylamide Copolymer 42

To a solution of pNAS (1.0 g, 5.91 mmol) in 50 mL DMF was added triethylamine (1.0 mL), followed by the dropwise addition of the L-fucose derivative 22 (356 mg, 1.18 mmol, 20 mol % with respect to pNAS). The solution was stirred at room temperature for 16 h, and subsequently heated to 40° C. for 18 h. The solution was cooled and isopropylamine (233 mg, 25 mol % with respect to pNAS) was added as a solution in DMF (1 mL). The solution was stirred at 40° C. for a further 24 h, followed by the addition of ethanolamine (2 mL, excess as a solution in 5 mL of DMF). The clear solution was stirred at room temperature for 12 h, followed by dialysis against water using dialysis tubing with a cut-off of 12,000–14,000 kD. The product was recovered by lyophilization. Yield 82%.

Example 15

Preparation of Fucose-Sialic Acid Acrylamide Copolymer 44

2-C-[3-[[2-aminoethyl]thio]propyl]-N-acetylneuraminic acid, 43, was prepared by the method described by Sparks et al., supra (1993).

A solution was prepared of pNAS (1.5 g, 8.87 mmol) in dimethylformamide (DMF, 60 mL). To this solution was added triethylamine (1.5 mL), followed by the dropwise addition of the L-fucose derivative 22 (534 mg, 1.77 mmol, 20 mol % with respect to pNAS). The solution was stirred at room temperature for 12 h, and subsequently heated to 40° C. for 24 h. The solution was cooled and the sialic acid derivative 43 (394 mg, 10 mol % with respect to pNAS) was added as a solution in DMF (5 mL). The solution was stirred at 40° C. for a further 24 h, followed by the addition of ethanolamine (2 mL, excess as a solution in 5 mL of DMF). The reaction mixture was stirred for 24 h at 40° C., cooled and precipitated into acetone (300 mL). The polymer was recovered by centrifugation, washed with acetone (10 mL) and the finely divided white solid dissolved in deionized water (10 mL) and dialysed against water for 24 h. The clear solution was lyophilized to dryness to give the desired product, 1.02 g, 72% yield.

Example 16

Preparation of Fucose-Sialic Acid Acrylamide Copolymer 45

A solution was prepared of pNAS (1.5 g, 8.87 mmol) in dimethylformamide (DMF, 60 mL). To this solution was added triethylamine (1.5 mL), followed by the dropwise addition of the L-fucose derivative 22 (534 mg, 1.77 mmol, 20 mol % with respect to pNAS). The solution was stirred at room temperature for 12 h, and subsequently heated to 40° C. for 24 h. The solution was cooled and the sialic acid derivative 43 (788 mg, 20 mol % with respect to pNAS) was added as a solution in DMF (5 mL). The solution was stirred at 40° C. for a further 24 h, followed by the addition of ethanolamine (2 mL, excess as a solution in 5 mL of DMF). The reaction mixture was stirred for 24 h at 40° C., cooled and precipitated into acetone (300 mL). The polymer was recovered by centrifugation, dissolved in deionized water (10 mL) and dialysed against water for 24 h. The clear solution was lyophilized to dryness to give the desired product, 1.44 g, 76% yield.

Example 17

Preparation of Galactosamine-Acrylamide Copolymer 47

Preparation of 2-acetamido-3,4,6-tri-O-acetyl-1-chloro-1,2-dideoxy-a-D-galactopyranose, 46

2-acetamido-2-deoxy-D-galactose (750 mg) was suspended in 4 ml of acetyl chloride in a tightly sealed flask and stirred 2°–4° C. until the solution became clear. The reaction mixture was diluted with 50 ml of cold dichlorometahne and 50 ml of cold water. The organic phase was dried over anhydrous sodium sulfate and the solvent was removed under vacuum to give 2-acetamido-3,4,6-tri-O-acetyl-1-chloro-1,2-dideoxy-a-D-galactopyranose, 46, as a white foam (1.0 g).

Preparation of 2-acetamido-3,4,6-tri-O-acetyl-1-azido-1,2-dideoxy-a-D-galactopyranose, 47

Compound 46 (950 mg) was added to a precooled solution of 1 g of sodium azide in 10 mL formamide. The mixture was stirred at room temperature for 24 hr. The reaction mixture was poured into a mixture of 50 mL of dichloromethane and 50 g of ice. The dichloromethane layer was collected and dried and the solvent was removed to give a gum. The gum was dissolved in 2 mL ethyl acetate and added dropwise to 100 mL hexane. Crystals of 2-acetamido-3,4,6-tri-O-acetyl-1-azido-1,2-dideoxy-a-D-galactopyranose 47, formed immediately and were collected by filtration (1.0 g).

Preparation of 2-acetamido-3,4,6-tri-O-acetyl-1-amino-1,2-dideoxy-a-D-galactopyranose, 48

Compound 47 (1.0 g) was dissolved in 30 mL methanol and subjected to hydrogenolysis using 1.0 g of 10% Pd on activated charcoal. After 24 hr, the charcoal was removed by filtration, and the filtrate was concentrated under vacuum to give 2-acetamido-3,4,6-tri-O-acetyl-1-amino-1,2-dideoxy-a-D-galactopyranose, 48, as colorless gum (850 mg). The derivative 48 gave a positive ninhydrin test.

Preparation of 2-acetamido-1-(N-CBZ-6-aminohexanamido)-3,4,6-tri-O-acetyl-1,2-dideoxy-a-D-galactopyranose, 49

6-N-Cbz-aminohexanoic acid (2.0 g) was dissolved in 20 mL dichloromethane and cooled in an ice bath. Dicyclohexylcarbodiimide (DCC, 1.3 g) was added to the cooled 6-N-Cbz-aminohexanoic acid solution, followed by a solution of the free base 48 (825 mg) in 10 mL dichloromethane. The reaction mixture was stirred at 5°–10° C. for 4 hr and then at room temperature for 16 hr. The precipitated dicyclohexylurea was removed by filtration. The filtrate was washed with 5% citric acid solution, followed by saturated sodium bicarbonate solution. The organic layer was dried over sodium sulfate and the solvent was removed under vacuum to give a white powder. The residue was chromatographed on silica gel column using hexane-ethyl acetate (1:1). Appropriate fractions were pooled and the solvent was removed to give 2-acetamido-1-(N-CBZ-6-aminohexanamido)-3,4,6-tri-O-acetyl-1,2-dideoxy-a-D-galactopyranose, 49, as a colorless foam (1.5 g). $^1$H NMR (CDCl$_3$): 7.35–7.40, s, 5H, C6H5CH2—; 5.7–5.8,m, 1H; 5.12, s, 2H, C6H5CH2; 4.45,m,1H; 3.8–3.88, m, 2H; 3.5–3.6,m,2H; 3.2–3.3,m, 2H; 2.23,s, 9H, OCOCH3; 2.21, s,3H;NHCOCH3; 1.5–1.7,m,10H.

Preparation of 2-acetamido-1-(N-CBZ-6-aminohexanaamido)-1,2-dideoxy-a-D-galactopyranose, 50

Compound 49 (1.4 g) was dissolved in methanol to which sodium methoxide-methanol solution was added dropwise to pH 11.0 and stirred at room temperature. The pH was adjusted to 11.0 with fresh sodium methoxide solution several times until the pH was stable (approximately 1 hr). The reaction mixture was acidified with Dowex-H type resin and the resin was removed from the solution by filtration. The solvent was removed from the filtrate under vacuum to give 2-acetamido-1-(N-CBZ-6-aminohexanamido)-1,2-dideoxy-a-D-galactopyranose, 50, as a gum (630 mg). $^1$H NMR (CDCl$_3$): $^1$H NMR (CD$_3$OD): 7.35–7.40, s, 5H, C6H5CH2—; 5.78–5.8,m, 1H; 5.12, s, 2H, C6H5CH2; 4.45–3.8, m, 6H; 3.65–3.6, m, 1H; 2.22,s, 3H; NHCOCH3; 1.5–1.7, m, 10H.

Preparation of 2-acetamido-1-(6-aminohexanamido)-1,2-dideoxy-a-D-alactopyranose, 51

To 500 mg of 10% Pd on activated charcoal, was added a solution of derivative 50 (800 mg in 25 mL methanol) and the mixture was subjected to hydrogenolysis on a Parr apparatus under 50 psig hydrogen for 4 hr. The charcoal was removed by filtration and the solvent was removed under vacuum. 2-acetamido-1-(6-aminohexanamido)-1,2-dideoxy-a-D-galactopyranose, 51, was obtained as a colorless gum (450 mg). $^1$H NMR (CD$_3$OD): 6.1, m, 1H; 4.6–4.8, m, 2H; 4.42–4.56,m,1H; 4.05–4.23, m, 2H; 3.8–3.98, m, 2H; 2.23, s, 3H; 1.9, m, 2H; 1.4–1.5, m, 6H.

Preparation of 2-acetamido-1-(6-acrylamidohexanamido)-1,2-dideoxy-a-D-galactopyranose, 52

The free base 51 (400 mg) was dissolved in a mixture of 1 mL water, 1 mL 2N sodium hydroxide solution and 0.1 mL of acryloyl chloride and the reaction mixture was stirred for 4 hr. The reaction mixture was acidified with 1N HCl and the volatiles were removed from the solution under vacuum. The resulting residue was chromatographed using 5% methanol in dichloromethane to give 52 as a colorless foam (150 mg).

Preparation of Galactosamine-acrylamide Copolymer, 53

Monomer 52 (150 mg, 0.4 mmol) and acrylamide (1.15 g, 1.6 mmol) were dissolved in 3 mL of water and purged with nitrogen for 5 min. The radical initiator V-50 (2.5 mg) was added to the reaction mixture and the solution was heated to 60° C. for 30 min. The solution became viscous during this period. The heating was discontinued and the reaction mixture was stirred for 24 hr at room temperature. The viscous solution was poured into 50 mL of isopropanol while stirring, causing the polymer to precipitate. The polymer was collected by filtration and dried under vacuum at room temperature to give 53 as a white powder (250 mg).

Example 18

Preparation of Sialic Acid-galactosamine Copolymer

Preparation of Succinimidyl 6-(N-benzyloxycarbonyl-amido)hexanoate, 54

6-(N-benzyloxycarbonylamido)hexanoic acid (27 g) was added to a cooled (5° C.) solution of N-hydroxysuccinimide (11.5 g) and 1-(3-dimethylaminopropyl)-3-ethylcarbodiimide hydrochloride in 300 mL methylene chloride under a nitrogen atmosphere. The reaction mixture was allowed to warm to room temperature and stirred for 4 hr. The reaction mixture was washed sequentially with 1N HCl (3×100 mL), saturated aqueous sodium bicarbonate solution (3×100 mL) and saturated aqueous sodium chloride solution. The organic layer was dried over sodium sulfate, filtered and evaporated to yield 54 as a colorless oil, yield 36 g.

Preparation of 2-(6-(N-benzyloxycarbonylamido)-hexanoylamido)-D-galactose, 55

Compound 54 (27 g, 75 mmol) and 2-amino-2-deoxy-D-galactose hydrochloride (10.78 g, 50 mmol) were dissolved in 100 mL methanol and cooled to 10° C. Triethylamine (14 mL, 100 mmol) was added dropwise. The reaction mixture was stirred for 4 hr., and then cooled to −20° C., causing the triethylamine salt to precipitate. The precipitate was removed by filtration. The solvent was removed under reduced pressure to give a solid white residue. The residue was partitioned between dichloromethane and water, and the aqueous layer was lyophilized to give a white powder (15 g).

Preparation of 2-(6-aminohexanoylamido)-D-galactose, trifluoroacetate salt, 56

Compound 55 (14 g, 30 mmol) was dissolved in a solution of 2 mL trifluroacetic acid in 60 mL methanol. The solution was subjected to hydrogenolysis in the presence of 10% Pd/C (2.0 g) at 50 psig for 6 hr. The charcoal was removed by filtration. The solvent was removed from the filtrate to give a semi-solid which was dried under vacuum at room temperature to afford 13.5 g of a white foam.

Preparation of Sialic Acid-galactosamine Copolymer, 57

A solution was prepared of pNAS (1.5 g, 8.87 mmol) in dimethylformamide (DMF, 60 mL). To this solution was added triethylamine (1.5 mL), followed by the dropwise addition of the galactosamine derivative 56 (720 mg, 1.77 mmol, 20 mol % with respect to pNAS). The clear yellow solution was stirred at room temperature for 24 h, and subsequently heated to 40° C. for 24 h. The sialic acid derivative 43 (788 mg, 20 mol % with respect to pNAS) was added as a solution in DMF (5 mL). The solution was stirred at 40° C. for a further 24 h, followed by the addition of ethanolamine (2 mL, excess as a solution in 5 mL of DMF). The reaction mixture was stirred for 24 h at 40° C., cooled and precipitated into acetone (300 mL). Polymer 57 was recovered by centrifugation, dissolved in deionized water (10 mL) and dialysed against water for 24 h. The clear solution was lyophilized to dryness to give the desired product, 2.03 g, 87% yield.

Example 19

Preparation of Fucose-Sialic Acrylamide Copolymer 59

2-C-[3-[[2-N-acryloylaminoethyl]thio]propyl]-N-acetylneuraminic acid, 58, was prepared by the method described by Sparks et al., supra (1993).

A solution was prepared of fucose monomer 14a (259 mg, 0.75 mmol), sialic acid monomer 48 (1.045 g, 2.25 mmol) and acrylamide (319 mg, 4.5 mmol) in water (2 ml). The solution was degassed by a stream of nitrogen, and to the clear solution was added V-50 (10 mg). The solution was heated to 60° C. for 24 h, cooled and dialysed directly against water using a dialysis tube with a molecular weight cut-off of 6000–8000. The polymer was recovered by freeze-drying.

Example 20

In Vivo Testing of Polymers

Polymers 16a, 16b, 17a, 17b, 18a, 18b, 23 and 32 have been tested in vivo in mice (Suckling Mouse Model). Newly born 5 day old suckling CD1 mice are randomized and inoculated by oral administration with 5 mL of virus. On the 1st day of post-infection, these mice were treated with 5 mL of polymer solutions orally 3 times a day for 4 days. Pure water was used as a control. Five days following the infection, the mice were sacrificed, intestines were isolated, washed and frozen (using dry ice). The intestines were homogenized in PBS and virus levels were quantitated by enzyme linked immunosorbent assay (ELISA) using a primary antibody raised in guinea pig and a peroxidase-linked goat anti-guinea pig secondary antibody. Results were plotted as OD values and compared with control treated mice to identify effective compounds. The results are shown in the Table below.

TABLE

Inhibition of Rotavirus Infection In Vivo. (Con. = Concentration)

| Polymer | | Con. Activity | | |
|---|---|---|---|---|
| Sugar | Spacer | Linkage | | (w/w) |
| L-fucose (16a) | aminohexyl | -O- α/β | 5% | <1% inhibition |
| D-fucose (16b) | aminohexyl | -O- α/β | 5% | <1% inhibition |
| D-fucose (16b) | aminohexyl | -O- α/β | 20% | 6 to 20% inhibition |
| D-fucose (18b) | tetraethylene-glycol | -O- α/β | 5% | <1% inhibition |
| L-fucose (18a) | tetraethylene-glycol | -O- α/β | 5% | 76–100% inhibition |
| L-fucose (17a) | tetraethylene-glycol | -O- α/β | 10% | 82–100% inhibition |
| D-fucose (17b) | triethylene-glycol | -O- α/β | 10% | <5% inhibition |
| L-fucose (23) | aminoethyl-thiopropyl | -C- -α- | 6% | 76 to 100% inhibition |
| Stalic acid (32) | aminohexyl | -O- | 9% | 76 to 100% inhibition |

Equivalents

Those skilled in the art will recognize or be able to ascertain using no more than routine experimentation many equivalents to the specific embodiments of the invention described herein. Such equivalents are intended to be encompassed in the scope of the following claims.

What is claimed is:

1. A pharmaceutical composition comprising a polymer characterized by a polymerized monomer of Formula I,

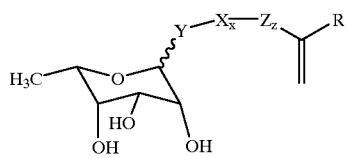

(I)

wherein
- x and z are each, independently, 0 or 1;
- the fucoside moiety is an α- or β-L-fucoside moiety or an α- or β-D-fucoside moiety;
- X is a straight chain or branched, substituted or unsubstituted alkylene group or an alkylene group wherein one or more carbon atoms is substituted by a heteroatom;
- Y is a CH$_2$ or NH group, or an oxygen or sulfur atom;
- Z is a carbonyl, amidocarbonyl, oxycarbonyl, phenylene, amino, or aminomethylene group, or an oxygen atom, provided that when x is 0 and Y is an oxygen or sulfur atom, Z is not an oxygen atom or an oxycarbonyl group; and
- R is a hydrogen atom or a methyl or ethyl group.

2. The pharmaceutical composition of claim 1 wherein X is selected from the group consisting of —(CH$_2$)$_6$—, —CH$_2$CH$_2$OCH$_2$CH$_2$OCH$_2$CH$_2$—, and —CH$_2$CH$_2$O(CH$_2$CH$_2$O)$_2$CH$_2$CH$_2$.

3. The pharmaceutical composition of claim 1 wherein the polymer is further characterized by a polymerized hydrophobic monomer.

4. The pharmaceutical composition of claim 3 wherein the polymerized hydrophobic monomer has a pendant hydrophobic group.

5. The pharmaceutical composition of claim 4 wherein the pendant hydrophobic group is a normal or branched, substituted or unsubstituted, C$_2$–C$_{18}$-alkyl group or an aryl group.

6. The pharmaceutical composition of claim 5 wherein the hydrophobic monomer is N-n-decylacrylamide or N-isopropylacrylamide.

7. The pharmaceutical composition of claim 3 further characterized by a polymerized neutral hydrophilic monomer.

8. The pharmaceutical composition of claim 7 wherein the neutral hydrophilic monomer is acrylamide or N-(2-hydroxyethyl)acrylamide.

9. The pharmaceutical composition of claim 1 wherein the monomer is of Formula II,

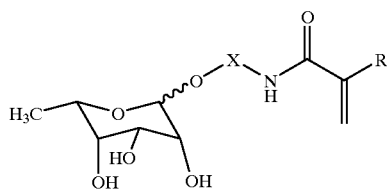

(II)

wherein R is a hydrogen atom or a methyl or ethyl group.

10. The pharmaceutical composition of claim 9 wherein X is selected from the group consisting of —(CH$_2$)$_6$—, —CH$_2$CH$_2$OCH$_2$CH$_2$OCH$_2$CH$_2$— and —CH$_2$CH$_2$O(CH$_2$CH$_2$O)$_2$CH$_2$CH$_2$.

11. The pharmaceutical composition of claim 10 wherein the monomer is of Formula III,

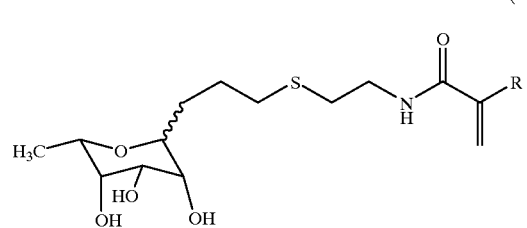

(III)

wherein R is a hydrogen atom or a methyl or ethyl group.

12. A pharmaceutical composition comprising a polymer characterized by a polymerized monomer of Formula VI,

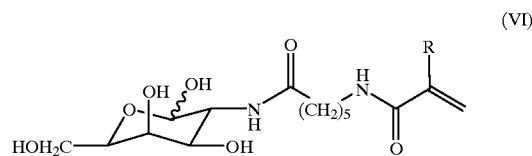

(VI)

wherein R is H, methyl or ethyl.

13. A pharmaceutical composition comprising a polymer characterized by a polymerized monomer of Formula VII,

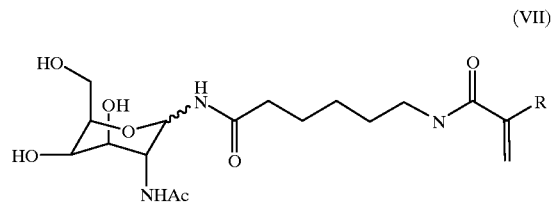

(VII)

wherein R is H, methyl or ethyl.

14. The pharmaceutical composition of claim 13 wherein the polymer is further characterized by a polymerized acrylamide monomer.

15. The pharmaceutical composition of claim 14 wherein the polymer comprises from about 20 mole percent to about 30 mole percent of a polymerized monomer of Formula I.

16. A pharmaceutical composition comprising a polymer characterized by a polymerized fucoside-bearing monomer and a polymerized sialic acid-bearing monomer.

17. A pharmaceutical composition comprising a polymer characterized by a polymerized fucoside-bearing monomer and a polymerized aminogalactose-bearing monomer.

18. A pharmaceutical composition comprising a polymer characterized by a polymerized sialic acid-bearing monomer and a polymerized aminogalactose-bearing monomer.

19. The pharmaceutical composition of claim 16 wherein the polymer is characterized by a polymerized monomer of Formula III (III)

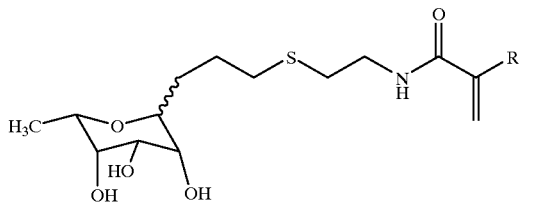

wherein R is a hydrogen atom or a methyl or ethyl group, and a polymerized monomer of Formula VIII, (VIII)

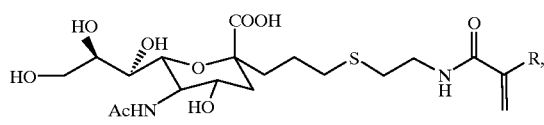

wherein R is a hydrogen atom or a methyl or ethyl group.

20. The pharmaceutical composition of claim 17 wherein the polymer is characterized by a polymerized monomer of Formula III, (III)

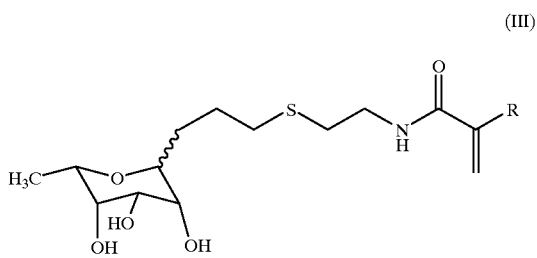

wherein R is a hydrogen atom or a methyl or ethyl group and a polymerized monomer of Formula VI, (VI)

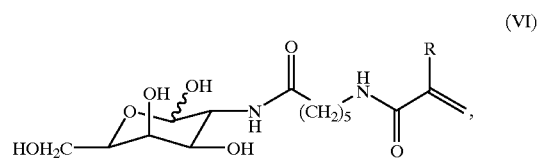

wherein R is H, methyl or ethyl.

21. The pharmaceutical composition of claim 18 wherein the polymer is characterized by a polymerized monomer of Formula VIII, (VIII)

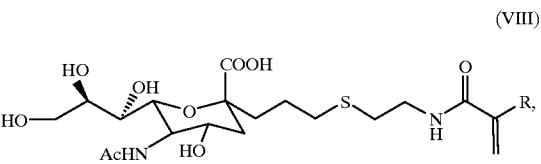

wherein R is a hydrogen atom or a methyl or ethyl group, and a polymerized monomer of Formula VI, (VI)

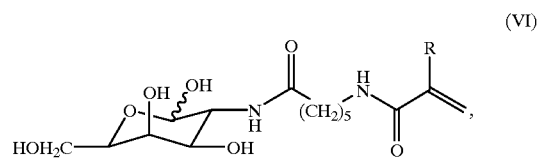

wherein R is H, methyl, or ethyl.

* * * * *